(12) United States Patent
Biedermann et al.

(10) Patent No.: US 7,731,749 B2
(45) Date of Patent: Jun. 8, 2010

(54) BONE ANCHORING DEVICE

(75) Inventors: Lutz Biedermann, VS-Villingen (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 320 days.

(21) Appl. No.: 11/599,676

(22) Filed: Nov. 15, 2006

(65) Prior Publication Data

US 2007/0161999 A1 Jul. 12, 2007

Related U.S. Application Data

(60) Provisional application No. 60/738,007, filed on Nov. 17, 2005.

(30) Foreign Application Priority Data

Nov. 17, 2005 (EP) ................................ 05025161

(51) Int. Cl.
- A61F 2/08 (2006.01)
- A61F 2/30 (2006.01)
- A61B 17/56 (2006.01)
- A61B 17/58 (2006.01)
- A61B 17/70 (2006.01)

(52) U.S. Cl. ..................................... 623/13.14; 606/254

(58) Field of Classification Search ....................... None
See application file for complete search history.

(56) References Cited

U.S. PATENT DOCUMENTS

| | | | |
|---|---|---|---|
| 5,443,467 A | 8/1995 | Biedermann et al. | |
| 6,302,410 B1 * | 10/2001 | Wentworth et al. | 279/152 |
| 6,540,748 B2 * | 4/2003 | Lombardo | 606/264 |
| 2003/0220642 A1 * | 11/2003 | Freudiger | 606/61 |
| 2004/0138660 A1 | 7/2004 | Serhan | |
| 2005/0096659 A1 | 5/2005 | Freudiger | |

(Continued)

FOREIGN PATENT DOCUMENTS

DE 4307576 C1 4/1994

(Continued)

OTHER PUBLICATIONS

European Search Report for European Application No. 05025161.0-2318 dated Mar. 21, 2006 and mailed Apr. 4, 2006, 6 pp.

*Primary Examiner*—Paul B Prebilic
*Assistant Examiner*—Jacqueline Woznicki
(74) *Attorney, Agent, or Firm*—Christie, Parker & Hale, LLP

(57) ABSTRACT

A bone anchoring device includes an anchoring element having a shank to be anchored in a bone or a vertebra and a head, a connection element for connecting at least two anchoring elements, a receiving part having a first end receiving the head, wherein the head is pivotable in the receiving part, and a second end comprising a recess for receiving the connection element, a first pressure element which exerts pressure on the head to lock the head in the receiving part, and a second pressure element which exerts pressure on the connection element to press the connection element against the first pressure element. The contour of the surface of at least the first pressure element or the second pressure element facing the connection element deviates from the contour of the surface of the connection element.

32 Claims, 2 Drawing Sheets

U.S. PATENT DOCUMENTS

2005/0131410 A1  6/2005  Lin
2007/0093820 A1  4/2007  Freudiger

FOREIGN PATENT DOCUMENTS

| | | | |
|---|---|---|---|
| EP | 1364622 | A2 | 11/2003 |
| EP | 13646622 | A2 | 11/2003 |
| EP | 1527742 | A1 | 5/2005 |
| WO | WO 98/27884 | A1 | 7/1998 |

* cited by examiner

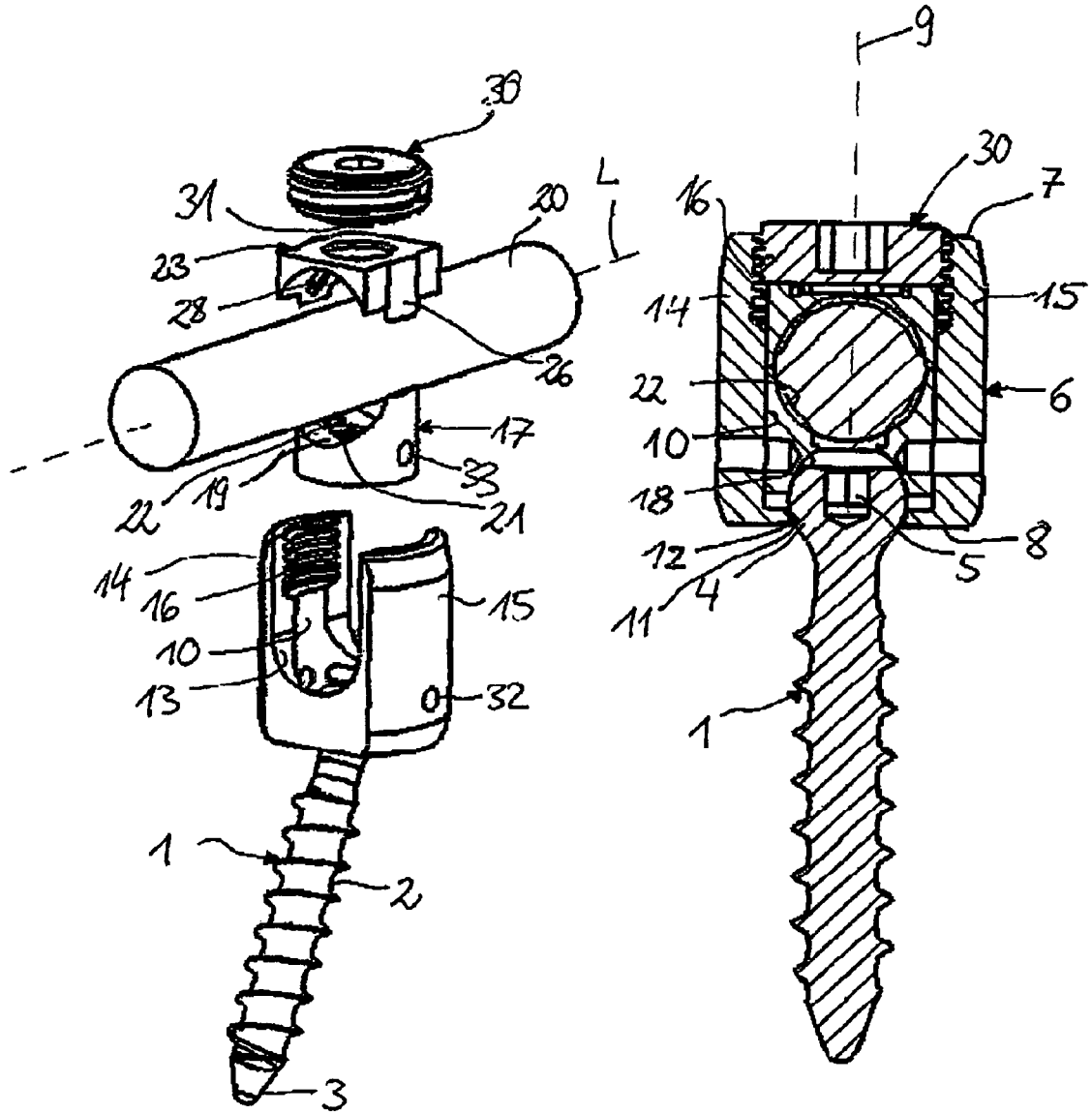

US 7,731,749 B2

BONE ANCHORING DEVICE

CROSS-REFERENCE TO RELATED APPLICATION(S)

The present disclosure claims the benefit of U.S. Provisional Patent Application Ser. No. 60/738,007, filed Nov. 17, 2005, and claims priority from European Patent Application EP05025161.0, filed Nov. 17, 2005, the entire disclosures of which are incorporated herein by reference.

FIELD OF DISCLOSURE

The present invention relates to a bone anchoring device for the dynamic stabilization of bones in particular for the dynamic stabilization of the spine. It includes a bone anchoring element which can be connected with a flexible rod made of an elastic material and allows a polyaxial adjustment of the position of the anchoring element relative to the rod.

BACKGROUND

A polyaxial bone screw to be connected with a stiff rod, usually made of metal, is known from DE 43 07 576 C1. When using a flexible rod made of an elastic material with such a bone screw, the pressure exerted by the inner fixation screw onto the rod would cause a deformation of the elastic material which could result in loosening of the fixation.

Bone anchoring devices comprising a bone screw and a flexible rod which is made of an elastic material are known from EP 1 364 622 A2 and EP 1 527 742 A1. The rod and the receiving part of the bone screw as well as the closure element comprise geometrically corresponding ribs and grooves in the surface to achieve a form-fit connection. Before fixation, the geometrically corresponding shapes of the rod and the bone screw have to be aligned. This makes the adjustment difficult and time consuming. Furthermore, the receiving part and the shaft of the bone screw are monoaxially connected which further limits the possibility of adjustment of the position of the shaft relative to the rod.

Based on the foregoing, there is a need for a bone anchoring device which can be used with a flexible connection element made of an elastic material and which allows a polyaxial adjustment of the position of the bone anchoring element relative to the rod while simultaneously providing a safe locking.

SUMMARY

During tightening of the closure element of the bone anchoring device according to the present disclosure, the deformation of the elastic material of the rod leads to a form-fit connection between the elastic rod and the receiving part. This provides an enhanced locking of the rod and furthermore the securing of the position of the bone anchoring element relative to the rod. Furthermore, a flow of the material of the rod in a direction along the longitudinal axis of the rod is minimized.

Further features and advantages of the disclosed bone anchoring device will become apparent and will be best understood by reference to the following detailed description of embodiments taken in conjunction with the accompanying drawings.

BRIEF DESCRIPTION OF THE DRAWINGS

FIG. 1 shows a perspective exploded view of a bone anchoring element according to the present disclosure.

FIG. 2 shows a sectional view of the bone anchoring device of FIG. 1 in an assembled state.

DETAILED DESCRIPTION

Figure 3A:
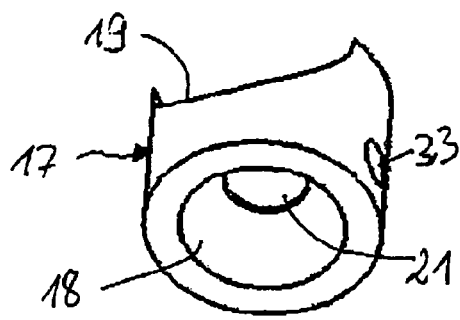
FIG. 3a shows a perspective view from below of a lower pressure element.

As shown in FIGS. 1 and 2, the bone anchoring device comprises a bone anchoring element 1 in the form of a bone screw having a shank 2 with a bone thread, a tip 3 at one end and a spherical head 4 at the opposite end. A recess 5 for engagement with a screwing-in tool is provided at the side of the head 4 which is opposite to the shank 2.

The bone anchoring device further includes a receiving part 6 having a first end 7 and a second end 8 opposite to the first end 7 and a longitudinal axis 9 intersecting the plane of the first end 7 and the second end 8. Coaxially with the longitudinal axis 9 a bore 10 is provided which extends from the first end 7 to a predetermined distance from the second end 8. At the second end 8 an opening 11 is provided the diameter of which is smaller than the diameter of the bore 10. A spherical section 12 is provided adjacent of the opening 10 which forms a seat for the spherical head 4.

The receiving part 6 further has a U-shaped recess 13 which starts at the first end 7 and extends in the direction of the second end 8 to a predetermined distance from the second end 8. By means of the U-shaped recess 13, two free legs 14, 15 are formed extending towards the first end 7. Adjacent to the first end 7, the receiving portion 6 includes an internal thread 16 at the legs 14, 15.

Further, there is provided a first pressure element 17 which has a cylindrical construction with an outer diameter which is only slightly smaller than the inner diameter of the bore 10 to allow the first pressure element 17 to be introduced into the bore 10 of the receiving part and to be moved in the axial direction. On its lower side facing towards the second end 8 the pressure element 17 includes a spherical recess 18 the radius of which corresponds to the radius of the spherical head 4 of the bone screw (see FIG. 3a and 5). On the side opposite its lower side, the first pressure element 17 has a cylindrical recess 19 which extends transversely to the longitudinal axis 9. The lateral diameter of this recess is selected such that a rod 20 with a circular cross section which is to be received in the receiving part can be inserted into the recess 19 and guided laterally therein. The depth of the cylindrical recess 19 is selected such that in an assembled state when the rod 20 is inserted and pressed against the bottom of the U-shaped recess 13, the first pressure element 17 exerts a pressure on the head 5. Further, the depth of the cylindrical recess 19 is preferably about half of the diameter of the rod 20.

Figure 5:
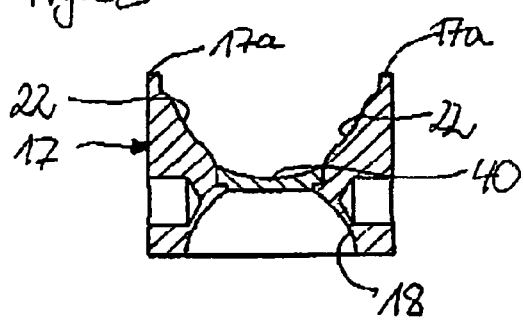
FIG. 5 shows a sectional view of a modified embodiment of a lower pressure element.

As can be seen in FIGS. 1, 3a and 5, the first pressure element 17 further has a coaxial bore 21 for guiding a screwing-in tool therethrough. On the surface of the first pressure element 17 which receives the rod 20, rib-like projections 22 are provided which extend in a direction transverse to the longitudinal axis L of the rod 20. A plurality of such projections 22 can be provided but a single projection is also sufficient. The projections 22 can have a structured shape which is able to press onto the smooth surface of the rod 20. As can be seen in FIG. 5, a cap 40 can be provided which fits into the coaxial bore 21 to close the coaxial bone 21 towards the cylindrical recess 19.

Figure 4A:
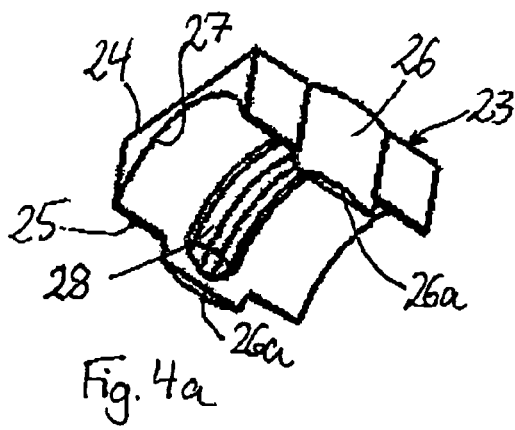
FIG. 4a shows a perspective view from below of an upper pressure element of the bone anchoring device.
Figure 3B:
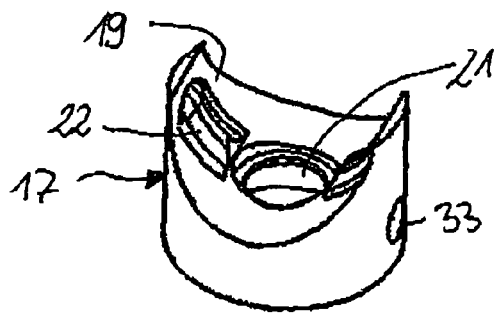
FIG. 3b shows a perspective view from above of a lower pressure element.
Figure 4B:
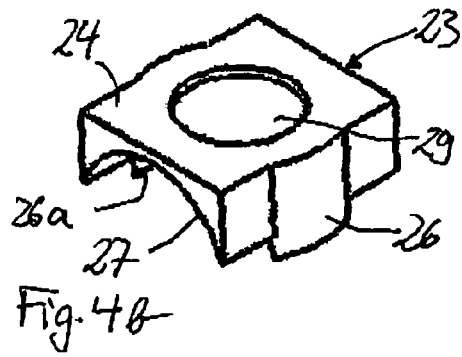
FIG. 4b shows a perspective view from the top of an upper pressure element.
Figure 3C:
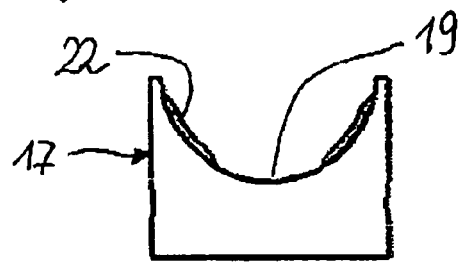
FIG. 3c shows a side view of a lower pressure element.
Figure 4C:
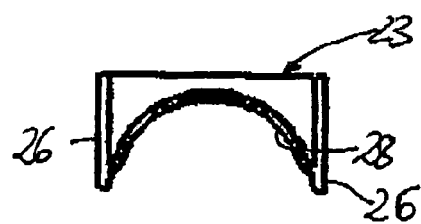
FIG. 4c shows a side view of an upper pressure element.

As shown in FIGS. 4a to 4c, the bone anchoring device comprises a second pressure element 23 of a substantially cuboidal shape with a substantially square shaped first end 24 and a second end 25. The width of the second pressure element is such that the second pressure element can be inserted into the U-shaped recess 13 of the receiving part 6. On its opposing lateral sides, the second pressure element includes two projections 26 shaped like a segment of a cylinder which fit into the space limited by the internal thread 16 to slide along the internal thread 16 when the second pressure element 23 is inserted.

The second pressure element 23 further includes a cylindrical recess 27 extending from the second end 25 in the direction towards the first end 24, the cylinder axis of which is perpendicular to that of the cylindrical projections 26. On the side of the second end 25, the cylindrical projections 26 include lower edges 26a. The diameter of the cylindrical recess 27 corresponds to the diameter of the rod 20 and its depth to half or less than half of the diameter of the rod 20. Similar to the first pressure element 17, one or more rib-like projections 28 are provided extending circumferentially on the surface of the recess 27 between the opposite cylindrical projections 26. The projections 28 have a structured shape which allows them to press onto the surface of the rod 20. The second pressure element 23 further has a coaxial bore 29.

The bone anchoring device further includes an inner screw 30 which can be screwed-in between the legs 14, 15. The inner screw 30 comprises a cylindrical projection 31 which can fit into the bore 29 of the second pressure element 23. The internal thread 16 and the cooperating thread of the inner screw 30 can have any known thread shape. A flat thread or a negative angle thread, however, can prevent splaying of the legs 14, 15.

The receiving part 6 and the first pressure element 17 include corresponding crimp bores 32, 33 on opposite sides by means of which the screw 1, the receiving part 6 and the first pressure element 17 can be loosely preassembled such that the first pressure element 17 is oriented with its cylindrical recess 19 coaxial with the U-shaped recess 13 of the receiving part 6.

The rod 20 can be made of an elastic material so that the rod 20 is partially or fully flexible. Preferably the rod 20 is made of a biocompatible plastic material, for example a polymer based on polyurethane or PEEK. The rod preferably has a smooth surface. The other parts of the bone anchoring device can be made of known biocompatible materials, such as stainless steel or titanium.

In use, the bone screw 1 of the pre-assembled bone anchoring device is screwed into the bone. To provide a stabilization structure, at least two bone anchoring devices which shall be connected by a rod 20 are anchored into the bone. Thereafter, the cap 40 is inserted into the coaxial bore 21 of the first pressure element 17 and the rod 20 is inserted between the legs 14 and 15. Then, the second pressure element 23 is inserted such that the first and the second pressure elements 17 and 23 encompass the rod 20 from both sides. After adjusting the angular position of the bone screw 1, the inner screw 30 is screwed-in between the legs 14, 15 until it contacts the first end 24 of the second pressure element 23. When the inner screw 30 is tightened, the second pressure element 23 is moved towards the first pressure element 17 until the lower edges 26a about onto the upper shoulders 17a. The cross-section of the space encompassed by the first and second pressure elements 17 and 23 is slightly smaller than the cross-section of the rod 20. Thus, the material from which the rod 20 is made begins to flow (i.e., plastic flow) allowing the projections 22, 28 to press onto the rod 20 which provides a firm, form-fit connection between the rod 20 and the first and second pressure elements 17 and 23 without destroying the integral structure of the rod 20. The cap 40 prevents the material of the rod 20 from flowing into the coaxial bore 21. At the same time, the first pressure element 17 is pressed onto the head 4 by the second pressure element 23 to lock the screw head 4 by means of friction in its rotational position. Preferably the projections 22, 28 extend perpendicular to the longitudinal direction L of the rod 20 to secure the rod 20 with respect to movements of the rod 20 in a direction along the longitudinal axis L.

As the locking of the rod 20 is achieved by pressing the projections 22, 28 onto the surface of the rod 20 without destroying the integral structure of the rod 20, secondary adjustments are possible.

Modifications of the above described embodiment are possible. For example, the rib-like projections 22, 28 can be provided only at one of the two elements, either the first pressure element 17 or the second pressure element 23. Instead of having rib-like projections provided at the surface of the first and the second pressure elements 17, 23 it is possible that on one pressure element, projections are formed and at the other pressure element corresponding recesses are formed. This allows the material which is displaced when the projections press onto the surface of the rod to flow into the corresponding recesses to generate a form-fit connection. Projections and recesses can be provided on both pressure elements 12, 23. The volumes of projections and recesses can be similar or have the same size such that after the flow of material is completed, the volume of the rod 20 in the region of the connection with the receiving part 6 has approximately the same size as before. Hence, the contact surface of the two pressure elements 17, 23 represents a cage encompassing the rod 20 preventing an uncontrolled flowing-out of material and thus maintains the overall length of the rod 20. This keeps the rod 20 safe in place. Projections and/or recesses need not to have a rib-like structure but can have any shape to achieve the desired function of a form-fit locking.

The rod 20 needs not to have a circular cross section. It can have an oval, rectangular or square cross section. The cap 40 can be omitted in case of rods 20 which have a sufficient stiffness. The elasticity of the rod 20 can vary. The rod 20 can be highly flexible or hardly flexible. The rod surface can be textured or structured.

For the inner screw 30, all known modifications can be used. This includes also the use of an outer ring or nut.

In the embodiment described, the bone anchoring element 1 is introduced from the top into the receiving part 6. However, the bone anchoring element 1 can also be introduced from the bottom of the receiving part 6 if the receiving part is constructed to allow such use.

The head 4 of the bone anchoring element 1, the shank 2, and/or the tip 3 can be constructed as separate parts which can be connected.

The invention is not limited to screws as bone anchoring elements but can be realized with bone hooks or any other bone anchoring element.

What is claimed is:

1. A bone anchoring device comprising:
   an anchoring element to be anchored to a bone or a vertebra and having a head;
   a connection element;

a receiving part having a first end receiving the head, wherein the head is pivotable in the receiving part, and a second end comprising a recess for receiving the connection element;
a first pressure element which exerts pressure on the head to lock the head in the receiving part;
a second pressure element which exerts pressure on the connection element to press the connection element against the first pressure element and wherein the second pressure element directly applies pressure to the first pressure element;
a closure element configured to exert pressure on the second pressure element;
wherein a contour of the surface of at least the first pressure element or the second pressure element facing the connection element deviates from a contour of the surface of the connection element; and
wherein the connection element is made of an elastic material.

2. The bone anchoring device of claim 1, wherein the connection element is a rod.

3. The bone anchoring device of claim 1, wherein the surface of the first and the second pressure elements facing the connection element deviate from the contour of the surface of the connection element.

4. The bone anchoring device of claim 1, wherein the deviation from the contour of the surface of at least the first pressure element or the second pressure element comprises any one of at least a projection and at least a recess.

5. The bone anchoring device of claim 1, wherein the deviation from the contour of the surface of at least the first pressure element or the second pressure element comprises any one of at least a rib structure and at least a pin structure.

6. The bone anchoring device of claim 1, wherein the first pressure element comprises a recess to receive the connection element and the second pressure element comprises a recess facing the connection element, wherein when pressure is exerted onto the second pressure element, the recesses form a cage structure encompassing the connection element.

7. The bone anchoring device of claim 6, wherein a cross-section of the cage structure is slightly smaller than a cross-section of the connection element.

8. The bone anchoring device of claim 1, wherein the deviation of the contour of the first pressure element or the second pressure element extends in a direction perpendicular to a longitudinal direction of the connection element.

9. The bone anchoring device of claim 4, wherein volumes of the projections and recesses are substsantially similar to each other.

10. The bone anchoring device of claim 1, wherein the first pressure element and the second pressure element comprise contact faces via which the first pressure element applies pressure to the second pressure element.

11. The bone anchoring device of claim 1, wherein a surface of the first pressure element facing the connection element extends above the recess of the receiving part in an assembled and tightened state.

12. The bone anchoring device of claim 1, wherein the connection element is constructed from a plastic material.

13. A bone anchoring device comprising:
an anchoring element to be anchored to a bone or a vertebra and having a head;
a connection element;
a receiving part having a first end receiving the head, wherein the head is pivotable in the receiving part, and a second end comprising a recess for receiving the connection element;
a first pressure element which exerts pressure on the head to lock the head in the receiving part;
a second pressure element which exerts pressure on the connection element to press the connection element against the first pressure element and wherein the second pressure element directly applies pressure to the first pressure element;
wherein a contour of the surface of at least the first pressure element or the second pressure element facing the connection element deviates from a contour of the surface of the connection element;
wherein the connection element is made of an elastic material; and
wherein a closure element is provided which closes the recess of the receiving part and which exerts onto the second pressure element.

14. A bone anchoring device comprising:
an anchoring element to be anchored to a bone or a vertebra and having a head;
an elastic connection element constructed from a plastic material;
a receiving part having a first end receiving the head, wherein the head is pivotable in the receiving part, and a second end comprising a recess for receiving the connection element;
a first pressure element having a recess and configured to exert pressure on the head to lock the head in the receiving part; and
a second pressure element having a recess and configured to exert pressure on the connection element to press the connection element against the first pressure element;
wherein the recess of the first pressure element and the recess of the second pressure element define a cage structure to receive the connection element;
wherein the second pressure element is moveable from a first position spaced apart from the first pressure element and contacting the connection element to a second position closer to the first pressure element; and
wherein at least a portion of the cage structure deviates from a contour of the surface of the connection element such that the portion of the cage structure plastically deforms a portion of the surface of the connection element in the second position of the second pressure element to interlock with the connection element.

15. The bone anchoring device of claim 14, wherein the connection element is a rod.

16. The bone anchoring device of claim 14, wherein the portion of the cage structure that deviates from the contour of the surface of the connection element is disposed on the recess of the first pressure element.

17. The bone anchoring device of claim 14, wherein the portion of the cage structure that deviates from the contour of the surface of the connection element is disposed on the recess of the second pressure element.

18. The bone anchoring device of claim 14, wherein the deviation of the portion of the cage structure comprises any one of at least a projection and at least a recess.

19. The bone anchoring device of claim 18, wherein volumes of the projections and recesses are substantially similar to each other.

20. The bone anchoring device of claim 14, wherein the deviation of the portion of the cage structure comprises any one of at least a rib structure or at least a pin structure.

21. The bone anchoring device of claim 14, wherein a cross-section of the cage structure is slightly smaller than a cross-section of the connection element.

22. The bone anchoring device of claim 14, wherein a closure element is provided which closes the recess of the receiving part and which exerts pressure onto the second pressure element.

23. The bone anchoring device of claim 14, wherein the deviation of the portion of the cage structure extends in a direction perpendicular to a longitudinal direction of the connection element.

24. The bone anchoring device of claim 14, wherein the first pressure element and the second pressure element comprise contact faces via which the second pressure element applies pressure to the first pressure element.

25. The bone anchoring device of claim 14, wherein a surface of the first pressure element facing the connection element extends above the recess of the receiving part in an assembled and tightened state.

26. A bone anchoring device comprising:
an anchoring element to be anchored to a bone or a vertebra and having a head;
an elastic connection element;
a receiving part having a first end receiving the head, wherein the head is pivotable in the receiving part, and a second end comprising a recess for receiving the connection element;
a first pressure element having a recess, the first pressure element configured to exert pressure on the head to lock the head in the receiving part; and
a second pressure element having a recess, the second pressure element configured to exert pressure on the connection element to press the connection element against the first pressure element;
wherein the surface of the recess of at least the first pressure element or the second pressure element facing the connection element deviates from the contour of the surface of the connection element; and
wherein the second pressure element contacts the first pressure element to apply pressure on the first pressure element.

27. The bone anchoring device of claim 26, wherein the surface of the recess of first pressure element and the surface of the recess of the second pressure element facing the connection element deviate from the contour of the surface of the connection element.

28. The bone anchoring device of claim 26, wherein the deviation from the contour of the surface of the recess of at least the first pressure element or the second pressure element comprises any one of at least a projection and at least a recess.

29. The bone anchoring device of claim 28, wherein volumes of the projections and recesses are substantially similar to each other.

30. The bone anchoring device of claim 26, wherein the deviation of the contour of the recess of the first pressure element or the second pressure element extends in a direction perpendicular to a longitudinal direction of the connection element.

31. The bone anchoring device of claim 26, wherein a surface of the first pressure element facing the connection element extends above the recess of the receiving part in an assembled and tightened state.

32. The bone anchoring device of claim 26, wherein the connection element is constructed from a plastic material.

* * * * *

UNITED STATES PATENT AND TRADEMARK OFFICE
CERTIFICATE OF CORRECTION

PATENT NO. : 7,731,749 B2  
APPLICATION NO. : 11/599676  
DATED : June 8, 2010  
INVENTOR(S) : Lutz Biedermann et al.

Page 1 of 1

It is certified that error appears in the above-identified patent and that said Letters Patent is hereby corrected as shown below:

In the Claims

| | |
|---|---|
| Column 5, Claim 9, line 48 | Delete "substsantially" <br> Insert -- substantially -- |
| Column 6, Claim 13, line 15 | After "exerts" <br> Insert -- pressure -- |
| Column 8, Claim 26, line 1 | Insert -- contour of the -- <br> Before "surface" |

Signed and Sealed this
First Day of March, 2011

David J. Kappos
*Director of the United States Patent and Trademark Office*